United States Patent
Austring

(10) Patent No.: US 12,242,499 B2
(45) Date of Patent: *Mar. 4, 2025

(54) SYSTEM AND METHOD OF ELECTRONIC HEALTH RECORD PERMISSIONING AND MONETIZATION

(71) Applicant: Synerio Technologies, Inc., Fort Worth, TX (US)

(72) Inventor: Ronald Raymond Austring, English Harbour (AG)

(73) Assignee: Technologies IP, LLC., Fort Worth, TX (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/730,851

(22) Filed: Apr. 27, 2022

(65) Prior Publication Data

US 2022/0343305 A1    Oct. 27, 2022

Related U.S. Application Data

(60) Provisional application No. 63/201,388, filed on Apr. 27, 2021, provisional application No. 63/201,386, (Continued)

(51) Int. Cl.
*G06F 16/25* (2019.01)
*G06F 16/27* (2019.01)
(Continued)

(52) U.S. Cl.
CPC ............ *G06F 16/258* (2019.01); *G06F 16/27* (2019.01); *G06F 21/6245* (2013.01);
(Continued)

(58) Field of Classification Search
CPC .... G06F 16/258; G06F 16/27; G06F 21/6245; G06F 2221/2141; G16H 10/60;
(Continued)

(56) References Cited

U.S. PATENT DOCUMENTS 8,612,363 B2 * 12/2013 Karkanias .............. G16H 40/67
706/11
8,790,255 B2 * 7/2014 Behar .................... A61B 5/744
345/473

(Continued)

FOREIGN PATENT DOCUMENTS

WO    WO-2019241166 A1 *  12/2019   ......... G06F 21/6245

OTHER PUBLICATIONS

Zhang, 2018, Elsevier, pp. 267-278.*
(Continued)

*Primary Examiner* — Michael I Ezewoko
(74) *Attorney, Agent, or Firm* — Whitaker Chalk Swindle & Schwartz PLLC; Enrique Sanchez, Jr.; Juan Vasquez

(57) ABSTRACT

A system and method for electronic health record permissioning and monetization that can grant or deny access to patient data and pay one or more entities for access to the data is presented. The present disclosure provides for a system configured to provide a patient the ability to: 'grant,' 'deny,' 'update,' and 'revoke' the permission to read data for a specific entity, and specific properties within that entity, from their personal data records (e.g., an electronic health record, a Global Patient Record (GPR), pharmaceutical records, demographic records, financial records, criminal records, or other suitable personal information). A Data-Read-Permission request can be a 'Property Collection' (PC) containing specific properties that describe the read permission rights and an amount the Data-Client is willing to offer for the Data-Read-Permission rights. This PC can be written as part of a blockchain transaction (TX1), which can be issued by the Data-Client.

20 Claims, 6 Drawing Sheets

Related U.S. Application Data filed on Apr. 27, 2021, provisional application No. 63/201,385, filed on Apr. 27, 2021, provisional application No. 63/201,387, filed on Apr. 27, 2021, provisional application No. 63/201,383, filed on Apr. 27, 2021.

(51) Int. Cl.

| | | |
|---|---|---|
| G06F 21/62 | (2013.01) | |
| G06Q 20/06 | (2012.01) | |
| G06Q 20/12 | (2012.01) | |
| G06Q 20/36 | (2012.01) | |
| G06Q 30/0283 | (2023.01) | |
| G16H 10/60 | (2018.01) | |
| H04L 9/00 | (2022.01) | |

(52) U.S. Cl.
CPC ....... *G06Q 20/065* (2013.01); *G06Q 20/1235* (2013.01); *G06Q 20/367* (2013.01); *G06Q 30/0283* (2013.01); *G16H 10/60* (2018.01); *H04L 9/50* (2022.05); *G06F 2221/2141* (2013.01); *H04L 2209/56* (2013.01)

(58) Field of Classification Search
CPC ..... H04L 9/50; H04L 2209/56; G06Q 20/065; G06Q 20/1235; G06Q 20/367; G06Q 30/0283

See application file for complete search history.

(56) References Cited

U.S. PATENT DOCUMENTS

| | | | | |
|---|---|---|---|---|
| 9,997,082 | B2* | 6/2018 | Kaleal | A61B 5/7445 |
| 10,204,384 | B2* | 2/2019 | Mehta | H04L 63/0861 |
| 10,296,297 | B2 | 5/2019 | Kumar et al. | |
| 10,373,466 | B1* | 8/2019 | St Amant | G06N 3/08 |
| 10,511,580 | B2* | 12/2019 | Isaacson | G06Q 20/401 |
| 10,643,266 | B2* | 5/2020 | Isaacson | H04W 12/08 |
| 10,825,111 | B2* | 11/2020 | Mehta | H04W 12/069 |
| 10,898,131 | B2* | 1/2021 | Iacoviello | A61B 5/165 |
| 10,909,638 | B2* | 2/2021 | Mehta | G06Q 50/01 |
| 11,080,777 | B2* | 8/2021 | Isaacson | G07F 9/006 |
| 11,093,911 | B2* | 8/2021 | Mallampalli | H04L 9/50 |
| 11,227,675 | B2* | 1/2022 | Bulleit | H04L 9/3268 |
| 11,259,729 | B2* | 3/2022 | St Amant | G16H 40/63 |
| 11,354,946 | B2* | 6/2022 | Pratz | G06Q 50/40 |
| 11,354,947 | B2* | 6/2022 | Pratz | H04L 9/50 |
| 11,397,728 | B2* | 7/2022 | Pandey | G06Q 10/10 |
| 11,423,712 | B2* | 8/2022 | Pratz | H04L 9/0637 |
| 11,522,703 | B1* | 12/2022 | Jain | H04L 9/0894 |
| 11,657,176 | B2* | 5/2023 | Bulleit | G06F 21/602 705/50 |
| 11,664,099 | B1* | 5/2023 | Jain | G16H 40/67 705/2 |
| 11,793,725 | B1* | 10/2023 | Badik | G16H 40/67 |
| 11,842,380 | B2* | 12/2023 | Isaacson | G06Q 50/01 |
| 11,903,725 | B2* | 2/2024 | Iacoviello | A61B 5/165 |
| 11,915,303 | B2* | 2/2024 | Isaacson | G06Q 20/12 |
| 11,990,233 | B2* | 5/2024 | Kaleal, III | G06Q 50/01 |
| 2003/0101169 | A1 | 5/2003 | Bhatt et al. | |
| 2012/0071771 | A1* | 3/2012 | Behar | G16H 40/67 600/300 |
| 2012/0127157 | A1* | 5/2012 | Adler | G06Q 10/00 345/419 |
| 2012/0182431 | A1* | 7/2012 | Asanov | A63F 13/335 348/207.1 |
| 2012/0271143 | A1* | 10/2012 | Aragones | G09B 5/02 600/595 |
| 2013/0178960 | A1* | 7/2013 | Sheehan | G16H 40/67 700/91 |
| 2013/0252731 | A1* | 9/2013 | Dugan | A63F 13/21 463/31 |
| 2014/0136237 | A1 | 5/2014 | Anderson et al. | |
| 2014/0188009 | A1* | 7/2014 | Lange | A61B 5/1128 600/595 |
| 2014/0379615 | A1 | 12/2014 | Brigham et al. | |
| 2016/0004820 | A1 | 1/2016 | Moore | |
| 2016/0077901 | A1 | 3/2016 | Roth et al. | |
| 2017/0161435 | A1 | 6/2017 | Orosco | |
| 2017/0212783 | A1 | 7/2017 | Choi et al. | |
| 2017/0235969 | A1 | 8/2017 | Kamara et al. | |
| 2018/0165416 | A1* | 6/2018 | Saxena | G16H 50/20 |
| 2019/0230070 | A1* | 7/2019 | Isaacson | H04W 12/084 |
| 2019/0306137 | A1* | 10/2019 | Isaacson | G06Q 50/01 |
| 2019/0354693 | A1 | 11/2019 | Yoon et al. | |
| 2020/0012676 | A1 | 1/2020 | Narang et al. | |
| 2020/0320061 | A1 | 10/2020 | Korpman et al. | |
| 2020/0374104 | A1* | 11/2020 | Heath | G06F 21/6245 |
| 2020/0382480 | A1* | 12/2020 | Isaacson | G06Q 20/384 |
| 2021/0358015 | A1* | 11/2021 | Isaacson | G07G 1/0036 |
| 2021/0365940 | A1* | 11/2021 | Tietzen | G06Q 20/12 |
| 2021/0375409 | A1* | 12/2021 | Romantsov | H04L 67/1097 |
| 2021/0383335 | A1* | 12/2021 | Mallampalli | H04L 9/50 |
| 2022/0188816 | A1* | 6/2022 | McFarlane | G06Q 20/40 |
| 2022/0345314 | A1* | 10/2022 | Doiron | G16B 50/50 |
| 2023/0351474 | A1* | 11/2023 | Isaacson | G06Q 20/384 |
| 2023/0360109 | A1* | 11/2023 | Isaacson | H04L 63/06 |
| 2024/0013283 | A1* | 1/2024 | Isaacson | G06Q 20/401 |
| 2024/0113728 | A1* | 4/2024 | Cooper | H03M 7/4056 |

OTHER PUBLICATIONS

PCT International Appl. No. PCT/US22/26593 International Search Report and Written Opinion, 7 pages, mailed Aug. 26, 2022.
PCT International Appl. No. PCT/US22/26605 International Search Report and Written Opinion, 8 pages, mailed Aug. 30, 2022.

* cited by examiner

| GPP Example | Derivation Path | Descripdtion |
|---|---|---|
| Patient.Prescriptions | m/100'/1' | Is the GPP to all of a Patient's Prescriptions. |
| Patient.Prescriptions.123456 | m/100'/1'/123456 | The GPP of a Specific Prescription |
| Patient.Prescriptions.123456.1 | m/100'/1'/123456/1 | The GPP of a Specific Prescription Fulfillment. |
| Patient.DeviceData.Heart.Apple.A59C3X | m/100'/2'/0/0/0 | The GPP of a Top-level Entity for all 'Apple' Heart Data for a Specific Serial # of a Watch. |

FIG. 2

SYSTEM AND METHOD OF ELECTRONIC HEALTH RECORD PERMISSIONING AND MONETIZATION

CROSS-REFERENCE TO RELATED APPLICATIONS

The present application claims priority to U.S. Provisional Patent Application Ser. No. 63/201,383, filed on Apr. 27, 2021, entitled "ADDRESSABLE UNIVERSAL DATA LOCATOR SYSTEM FOR PROGRAM EXECUTION AND METHOD THEREFOR," U.S. Provisional Patent Application Ser. No. 63/201,385, filed on Apr. 27, 2021, entitled "ELECTRONIC HEALTH RECORD PERMISSIONING SYSTEM AND METHOD," U.S. Provisional Patent Application Ser. No. 63/201,388, filed on Apr. 27, 2021, entitled "ELECTRONIC HEALTH RECORD DATA QUALIFICATION SYSTEM AND METHOD," U.S. Provisional Patent Application Ser. No. 63/201,387, filed on Apr. 27, 2021, entitled "SERVER PROTOCOL FORMATTING SYSTEM AND METHOD," and U.S. Provisional Patent Application Ser. No. 63/201,386, filed on Apr. 27, 2021, entitled "PROPERTY COLLETION SYSTEM AND METHOD," the contents of which are incorporated herein in their entireties for all purposes.

TECHNICAL FIELD

The present disclosure generally relates to data access permissioning, and more specifically to an electronic health record access permissioning and monetization.

BACKGROUND

Traditional patient record systems functions as conventional databases with data being stored in database tables associated with a particular patient. Although modern approaches indicate that the patient's data in their electronic health record belongs to the patient, there are limitations to the implementation of this statement. For example, these conventional databases systems do not empower the patient to control access to it data, nor do these systems provide the granularity of access rights to allow a patient to control exactly which data the system provides to third parties. Further, patients are not provided any incentive to provide their data to, for example, third-party researchers looking for a large enough sample space to verify their work.

SUMMARY

The present disclosure achieves technical advantages as a system and method for electronic health record permissioning and monetization that can grant or deny access to patient data and pay one or more entities for access to the data. The present disclosure provides for a system integrated into a practical application with meaningful limitations to provide a patient the ability to 'grant,' 'deny,' 'update,' and 'revoke' the permission to read data for a specific entity, and specific properties within that entity, from their personal data records (e.g., an electronic health record, a Global Patient Record (GPR), pharmaceutical records, demographic records, financial records, criminal records, or other suitable personal information). In one embodiment, a Data-Client can be a client that is requesting permission to use a Patient's data; a Patient can be a person having data stored in a record (e.g., a patient having an electronic health record stored in the GPR); an EHR-entity can be an entity within the GPR; an EHR-sub-entity can be a sub entity within the GPR (e.g., patient address, patient allergy, etc.); and a Utility can be a system providing the functionality disclosed herein.

The present disclosure solves the technological problem of organizing, accessing, and processing patient data stored in memory, as well as processing electronic offers for patient data access and facilitating a payment transaction to one or more entities once access is granted. The electronic health record permissioning and monetization system solves the aforementioned technological problem by providing a blockchain, transaction blockchain API, permissioning module, and a wallet module. Such modules can be implemented in one or more servers coupled to memory (local, network, distributed, or otherwise) using one or more private key pairs. Accordingly, the claims herein are necessarily rooted in computer technology as they overcome a problem arising in the realm of computer database storage, access permissions, encryption, and electronic payment.

The present disclosure provides a technological solution missing from conventional systems by providing a system that allows a patient the ability to: 'grant,' 'deny,' and 'revoke' the permission to read data for a specific entity, and specific properties within that entity, from their personal records. In one embodiment, access to the data can be facilitated via public-private key pairs. For example, a Utility can manage and store a Data-Client's private key. A Data-Read-Permission request can be a 'Property Collection' (PC) containing specific properties that describe the read permission rights and an amount the Data-Client is willing to offer for the Data-Read-Permission rights. This PC can be written as part of a blockchain transaction (TX1), which can be issued by the Data-Client, as Output-1.1. The TX1 transaction will have a second output (Output-1.2) that can pay an enticement to consider offer amount to the electronic currency address of the Patient, from which the Data-Client is seeking permission.

The concepts taught by the present disclosure can be used in any data-centric industry but are particularly relevant in the healthcare industry (e.g. clinincal, pharmaceutical, etc.). In another embodiment, National Council for Prescription Drug Programs (NCPDP) promulgates script standards that can support prior authorization transactions between a prescriber and a payer. Pursuant to such standards, the GPR can eliminate the need for these transactions by allowing the Payer to query the information that it needs directly from the Utility. The data contained in the GPR will be much richer than the data that can be obtained from the prescriber. The present disclosure provides a model where the Utility can interact with the payer when it runs edits for new prescriptions as part of the prescriber workflow, and when it runs edits for refills as part of the Pharmacy workflow.

Accordingly, the present disclosure discloses concepts inextricably tied to computer technology such that the present disclosure provides the technological benefit of optimizing database technology to allow a patient the ability to pick which information to share, as well as provide a technological utility to determine and provide such access. The present disclosure technologically surpasses conventional technology as, the Utility can prompt a patient to accept or deny a request for access and facilitate electronic payment for the access to the patient's data.

It is an object of the invention to provide a system for record access permissioning and monetization. It is a further object of the invention to provide a method of record access permissioning and monetization. These and other objects are provided by the present disclosure, including at least the following embodiments.

In one embodiment, a system for record access permissioning and monetization can include: a blockchain storing one or more data records; and a computer processor operably coupled to the blockchain and capable of executing machine-readable instructions to perform program steps, the program steps comprising: receiving a write permission request from a client indicating types of data to be accessed and an offer amount for access; instantiating a first blockchain transaction for requesting access permission to a person's record; writing the write permission request to the blockchain as part of the first block chain transaction; transferring the offer amount to a first blockchain address associated with the person as part of the first block chain transaction; determining that permission to access a record was granted by the person and instantiating a second blockchain transaction for granting permission; instantiating a third blockchain transaction for accepting permission; and paying the person the offer amount. Wherein the program steps further comprise transferring the offer amount having the first blockchain address to a second blockchain address associated with the patient as part of the second blockchain transaction. Wherein the program steps further comprise transferring a utility amount to a blockchain address associated with a data client as part of the second blockchain transaction. Wherein the person is paid the offer amount less the utility amount. Further comprising a transaction blockchain API configured to provide access to data stored on the blockchain. Wherein the transaction blockchain API includes an interface that defines interactions between multiple components. Wherein the write permission request is a Property Collection (PC). Wherein the write permission request Property Collection contains the write permission rights. Wherein the write permission request Property Collection contains the offer amount. Further comprising a wallet module configured to facilitate an electronic financial transaction over an encrypted network.

In another embodiment, a method of record access permissioning and monetization can include: receiving a write permission request from a client indicating types of data to be accessed and an offer amount for access; instantiating a first blockchain transaction for requesting access permission to a person's record; writing the write permission request to a blockchain as part of the first block chain transaction; transferring the offer amount to a first blockchain address associated with the person as part of the first block chain transaction; determining that permission to access a record was granted by the person and instantiating a second blockchain transaction for granting permission; instantiating a third blockchain transaction for accepting permission; and paying the person the offer amount. Further comprising transferring the offer amount having the first blockchain address to a second blockchain address associated with the patient as part of the second blockchain transaction. Further comprising transferring a utility amount to a blockchain address associated with a data client as part of the second blockchain transaction. Wherein the person is paid the offer amount less the utility amount. Further comprising a transaction blockchain API configured to provide access to data stored on the blockchain. Wherein the transaction blockchain API includes an interface that defines interactions between multiple components. Wherein the write permission request is a Property Collection (PC). Wherein the write permission request Property Collection contains the write permission rights. Wherein the write permission request Property Collection contains the offer amount. Further comprising a wallet module configured to facilitate an electronic financial transaction over an encrypted network.

BRIEF DESCRIPTION OF THE DRAWINGS

The present disclosure will be readily understood by the following detailed description, taken in conjunction with the accompanying drawings that illustrate, by way of example, the principles of the present disclosure. The drawings illustrate the design and utility of one or more exemplary embodiments of the present disclosure, in which like elements are referred to by like reference numbers or symbols. The objects and elements in the drawings are not necessarily drawn to scale, proportion, or precise positional relationship. Instead, emphasis is focused on illustrating the principles of the present disclosure.

FIG. 2 illustrates a table listing Global Patient Record Property Path mapping examples, in accordance with one or more exemplary embodiments of the present disclosure;

DETAILED DESCRIPTION

The disclosure presented in the following written description and the various features and advantageous details thereof, are explained more fully with reference to the non-limiting examples included in the accompanying drawings and as detailed in the description. Descriptions of well-known components have been omitted to not unnecessarily obscure the principal features described herein. The examples used in the following description are intended to facilitate an understanding of the ways in which the disclosure can be implemented and practiced. A person of ordinary skill in the art would read this disclosure to mean that any suitable combination of the functionality or exemplary embodiments below could be combined to achieve the subject matter claimed. The disclosure includes either a representative number of species falling within the scope of the genus or structural features common to the members of the genus so that one of ordinary skill in the art can recognize the members of the genus. Accordingly, these examples should not be construed as limiting the scope of the claims.

A person of ordinary skill in the art would understand that any system claims presented herein encompass all of the elements and limitations disclosed therein, and as such, require that each system claim be viewed as a whole. Any reasonably foreseeable items functionally related to the claims are also relevant. Pursuant to Section 904 of the Manual of Patent Examination Procedure, the Examiner, after having obtained a thorough understanding of the invention disclosed and claimed in the nonprovisional application has searched the prior art as disclosed in patents and other published documents, i.e., nonpatent literature. Therefore, as evidenced by the issuance of this patent, the prior art fails to disclose or teach the elements and limitations presented in the claims as enabled by the specification and drawings, such that the presented claims are patentable under 35 U.S.C. §§ 101, 102, 103, and 112.

Figure 1:
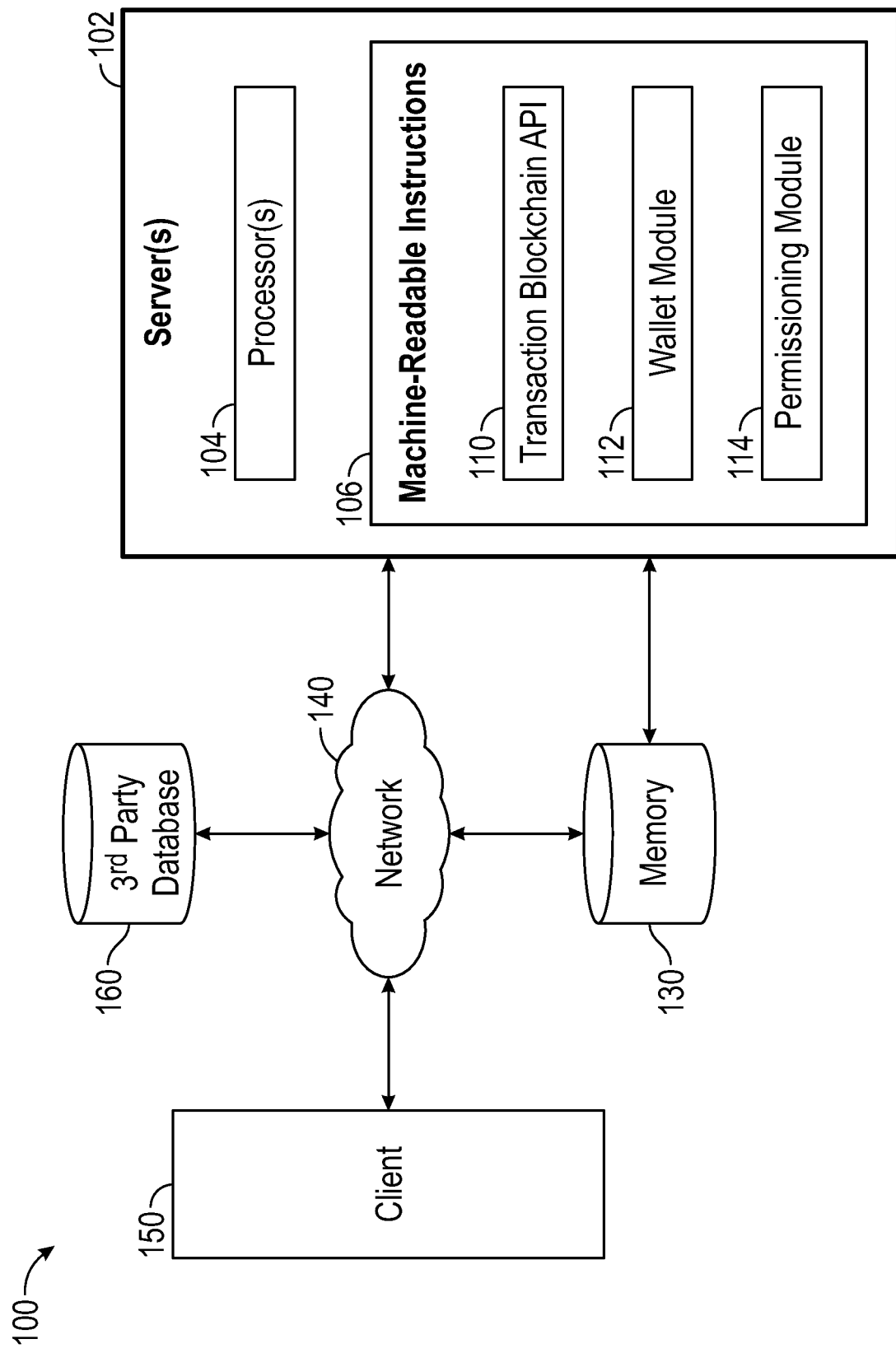
FIG. 1 illustrates an electronic health record permissioning and monetization system schematic, in accordance with one or more exemplary embodiments of the present disclosure.

FIG. 1 illustrates an electronic health record permissioning and monetization system 100 schematic, in accordance with one or more exemplary embodiments of the present disclosure. The system 100 can include one or more servers 102 having one or more processors 104, a memory 130, machine readable instructions 106, including transaction blockchain API 110, a wallet module 112, and a permissioning module 114, among other relevant modules. The server 102 can be operably coupled to one or more clients 150 via a network 140. The clients can be a physical device (e.g., mobile phone, laptop, tablet, desktop computer, wearable device, or other suitable device), program, or application. In another exemplary embodiment, a client can include a mobile phone having a mobile application configured to communicate with the server 102 over the network 140.

In one embodiment, a transaction blockchain API 110 can be provided by the system 100 for accessing the blockchain, the transaction blockchain API 110 having an interface that defines interactions between multiple components. For example, the blockchain API 110 can define the kinds of calls or requests that can be made, how to make them, the data formats that should be used, the conventions to follow, and other suitable functionality related to a blockchain. In another embodiment, the blockchain API 110 can access and retrieve Property Collections.

In one embodiment, a wallet module 112 can be a service or program that allows one party to make electronic transactions with another party bartering digital currency units for goods and services. This can include purchasing items on-line with a computer or using a smartphone to purchase something at a store. Money can be deposited in the digital wallet prior to any transactions or, in other cases, an individual's bank account can be linked to the digital wallet. Users might also have their driver's license, health card, loyalty card(s), and other ID documents stored within the wallet. The wallet module 112 can receive data from a client to effect an electronic funds transfer via ACH, bank wire, PayPal®, Venmo®, crypto currency (e.g., Bitcoin®, Doge®, Litecoin®, etc.). In another embodiment, the wallet module 112 can receive data related to a user's cryptocurrency address, or the holder's credentials. For example, the wallet module 112 could store a public-private key pair, or just a private key for a user of the system. See description related to FIG. 2, below. In another embodiment, the wallet module 112 can provide for a plurality of encryption standard or interfaces. For example, a Private Key (PK) interface allows the Data-Client to be in charge of their own Private Keys; a Token Key (TK) interface could use a simple client-specific access token (GUID); and a Client Certificate (CC) interface could rely on the fact that the client installed a client certificate. In another embodiment, the wallet module 112 can be configured to facilitate an electronic financial transaction over the encrypted network 140.

In one embodiment, the permissioning module 114 can provide control logic to allow a patient the ability to: 'grant,' 'update,' and 'revoke' permission to read data for a specific entity (e.g., Data-Client), and specific properties within that entity, from their personal data records, as detailed below.

The aforementioned systems, components, and modules can be communicably coupled to each other via the network 140, such that data can be transmitted therebetween. The network 140 can be the Internet, intranet, computer bus, or other suitable network. The data transmission can be encrypted, unencrypted, over a VPN tunnel, or other suitable communication means. The network 140 can be a WAN, LAN, PAN, or other suitable network type. The network communication can be encrypted using PGP, Blowfish, Twofish, AES, 3DES, HTTPS, or other suitable encryption. The system 100 can be configured to provide communication via the various systems, components, and modules disclosed herein via an application programming interface (API), PCI, PCI-Express, ANSI-X12, Ethernet, Fiber, Wi-Fi, Bluetooth, or other suitable communication protocol or medium. Additionally, third party systems and databases 160 can be operably coupled to the system components via the network 140.

The data transmitted to and from the components of system 100 (e.g., the server 102, memory 130, and clients 150), can include any format, including the XPP format disclosed herein, JavaScript Object Notation (JSON), TCP/IP, XML, HTML, ASCII, SMS, CSV, representational state transfer (REST), or other suitable format. The data transmission can include a message, flag, header, header properties, metadata, and/or a body, or be encapsulated and packetized by any suitable format having same.

The server(s) 102 can be implemented in hardware, software, or a suitable combination of hardware and software therefor, and may comprise one or more software systems operating on one or more servers, having one or more processors 104, with access to memory 130. Server(s) 102 can include electronic storage, one or more processors, and/or other components. Server(s) 102 can include communication lines, connections, and/or ports to enable the exchange of information via a network 140 and/or other computing platforms. Server(s) 102 can also include a plurality of hardware, software, and/or firmware components operating together to provide the functionality attributed herein to server(s) 102. For example, server(s) 102 can be implemented by a cloud of computing platforms operating together as server(s) 102, including Software-as-a-Service (SaaS) and Platform-as-a-Service (PaaS) functionality. Additionally, the server(s) 102 can include memory 130, locally attached, network attached, or both.

Memory 130 can comprise electronic storage that can include non-transitory storage media that electronically stores information. The electronic storage media of electronic storage can include one or both of system storage that can be provided integrally (e.g., substantially non-removable) with server(s) 102 and/or removable storage that can be removably connectable to server(s) 102 via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). The electronic storage can include a database, or public or private distributed ledger (e.g., blockchain). In one embodiment, memory 130 can be a blockchain implemented on one or more platforms, including BigChainDB, nChain, Ethereum, Hyperledger, R3, Ripple, EOS, or other suitable blockchain platform. The blockchain can be a public blockchain (accessible to the general public)

or a private blockchain (accessible only by those parties credentialed for access). Electronic storage can store machine-readable instructions 106, software algorithms, control logic, data generated by processor(s), data received from server(s), data received from computing platform(s), and/or other data that can enable server(s) to function as described herein. The electronic storage can also include third-party databases accessible via the network 140.

Processor(s) 104 can be configured to provide data processing capabilities in server(s) 102. As such, processor(s) 104 can include one or more of a digital processor, an analog processor, a digital circuit designed to process information, an analog circuit designed to process information, a state machine, and/or other mechanisms for electronically processing information, such as FPGAs or ASICs. The processor(s) 104 can be a single entity or include a plurality of processing units. These processing units can be physically located within the same device, or processor(s) 104 can represent processing functionality of a plurality of devices or software functionality operating alone, or in concert.

The processor(s) 104 can be configured to execute machine-readable instructions 106 or machine learning modules via software, hardware, firmware, some combination of software, hardware, and/or firmware, and/or other mechanisms for configuring processing capabilities on processor(s) 104. As used herein, the term "machine-readable instructions" can refer to any component or set of components that perform the functionality attributed to the machine-readable instructions component 106. This can include one or more physical processors 104 during execution of processor-readable instructions, the processor-readable instructions, circuitry, hardware, storage media, or any other components.

The server(s) 102 can be configured with machine-readable instructions having one or more functional modules. The machine-readable instructions 106 can be implemented on one or more servers 102, having one or more processors 104, with access to memory 130. The machine-readable instructions 106 can be a single networked node, or a machine cluster, which can include a distributed architecture of a plurality of networked nodes. The machine-readable instructions 106 can include control logic for implementing various functionality, as described in more detail below. The machine-readable instructions 106 can include certain functionality associated with the system 100. Additionally, the machine-readable instructions 106 can include a smart contract or multi-signature contract that can process, read, and write data to the memory 130, 3rd party database 160, including a database, distributed ledger, or blockchain. In another embodiment, the Utility can be implemented via the one or more server(s) 102.

FIG. 2 illustrates a table 200 listing Global Patient Record Property Path mapping examples, in accordance with one or more exemplary embodiments of the present disclosure. The table 200 lists a GPP example 202, an associated derivation path 204, and a description 206. In one embodiment, a GPR Entity can be data, encapsulated within a Property Collection, within a Patient's GPR. The address to the entity can be described by a Global Patient Record Property Path (GPP). This path can be relative to a specific patient. In another embodiment, a hierarchical deterministic (HD) wallet can use derivation paths to specify an address to a keypair within the hierarchy. An HD wallet can be patient specific and used to manage a patient's public and private keys. As its name suggests there is one root key that can have child keys, with each child key having their own children. This can keep repeating into a large hierarchy. In one embodiment, an HD Wallet can automatically generate a hierarchical tree-like structure of private/public addresses (or keys), thereby addressing the problem of the user having to generate them on their own. In another embodiment, a GPP can be mapped to a derivation path. This mapping can associate a GPP with a keypair. As shown in table 200, the GPP 202 can be mapped to an HD Wallet Derivation Path 204.

In another embodiment, the Utility can implement a hierarchical deterministic wallet, in combination with Metanet technology to create the structure and storage for a Patient's GPR. For example, a Metanet can be a global protocol and framework for structuring and facilitating the on-chain internet for a BitcoinSV blockchain. In particular, the Metanet can be a protocol for creating transactions that allow on-chain data to form a graph structure, which can be interpreted and used off-chain by wallets, browsers, and applications. This metanet, coupled with a built-in permissioning system according to the present disclosure, can use the stable, underlying protocol of a BSV blockchain to ensure users and content creators are in complete control and own their data.

Figure 3:
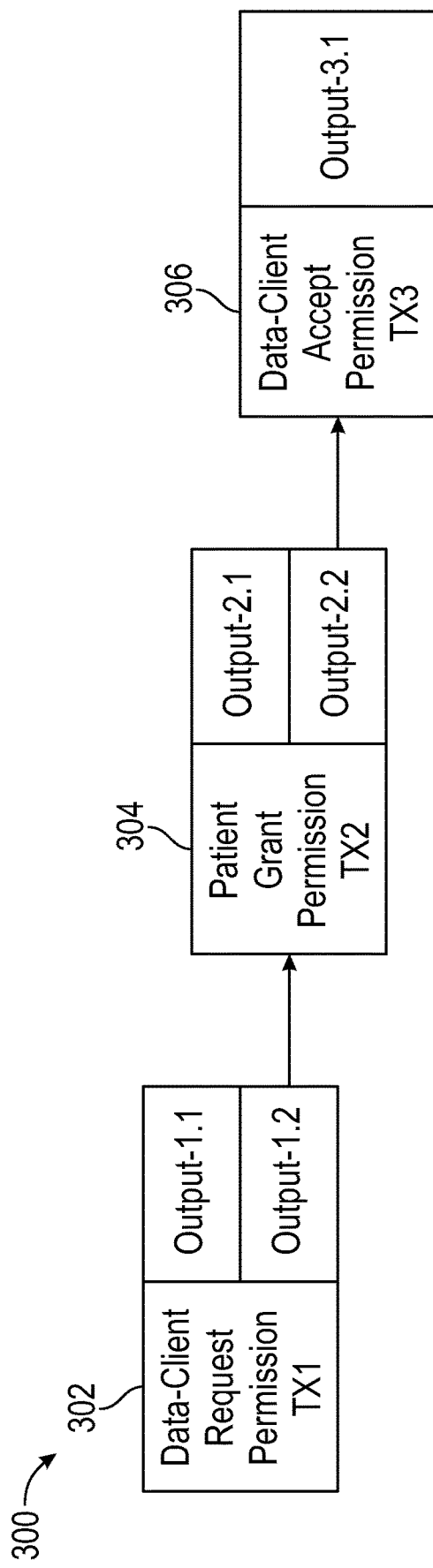
FIG. 3 illustrates a data request-grant-accept schematic, in accordance with one or more exemplary embodiments of the present disclosure.

FIG. 3 illustrates a data request-grant-accept schematic 300, in accordance with one or more exemplary embodiments of the present disclosure. In one embodiment, the Patient has the ability to 'grant' permission to read data for a specific entity, and specific properties within that entity, from their GPR. For example, if the Patient decides to grant the permission, the permissioning module can process data as follows: generation of a Data-Client Request Permission blockchain transaction (TX1) 302 having an Output-1.1 and Output-1.2; generation of a Patient Grant Permission blockchain transaction (TX2) 304 having an Output-2.1 and Output-2.2; and generation of a Data-Client Accept Permission blockchain transaction (TX3) 306 having an Output-3.1.

In another embodiment, a Data-Read-Permission request can be a 'Property Collection' (PC) containing specific properties that describe the read permission rights and an amount the Data-Client is willing to offer for the Data-Read-Permission rights. This PC can be written as part of a Data-Client Request Permission blockchain transaction (TX1) 302, which can be issued by the Data-Client, as Output-1.1. The TX1 transaction 302 can have a second output (Output-1.2) that can pays an enticement to consider offer amount to the blockchain address of the Patient, from which the Data-Client is seeking permission. In another embodiment, if the Patient decides to grant the permission, the permissioning module can issue another blockchain transaction (TX2) 304, with two outputs, that spends Output-1.2 of TX1 302 and pays a nominal amount to the Data-Client or Utility through Output-2.2 of TX2 304. The Output-2.1 can be a data output, which contains a Property Collection (PC) with property values that specify that the permission has been granted. The TX2 transaction 304 can also send money to another blockchain address of the Patient (e.g., spending the enticement to consider amount). The Data-Client can then write another blockchain transaction (TX3) 306, which can spend Ouput-2.2 of TX2 and pay the Patient the offer amount for the Data-Read-Permission. In another embodiment, the transaction TX3 can verify a contract granting access and paying the enticement amount. For example, these blockchain transactions can represent the Data-Read-Permission Contract between the Data-Client and the Patient. This contract will be verified when the Data-Client issues a request for the data (via Output-3.1) for which the Data-Read-Permission was granted. In another embodiment, one or more of the following ReadPermission Property Collection attributes can be used during this process:

| Name | Type | Description |
| --- | --- | --- |
| RID | String | A GUID that will be used as the read permission ID. |
| Type | String | "r"-Read |
| PublicKey | byte array | A public key representing an ID for the patient. The patient's root public key is not exposed. |
| GPP | string | The GPP of the entity in which the permission applies. |
| GPP_Properties | Property Collection Array | A collection of PropertyPermission structures that define the specific properties of an entity that are accessible. |
| GPP_Children | Boolean | A Boolean value that indicates if the permission is being granted to all child nodes of the GPP. |
| FromDateTime | DateTime | A DateTime value used to indicate the minimum Date and Time of when the data starts. If this field is not present, then all data from beginning of data until ToDateTime will be used. |
| ToDateTime | DateTime | A DateTime value used to indicate the maximum Date and Time of the data of when the date ends. If this property is not present, then all data FromDateTime will be used. |
| ReadDataFunction | String | The name of a data retrieval function used to extract the GPR Entity(s) and package it for the Data-Client. |
| ReadDataQualifier | String | The name of a qualifier used to filter data as it is retrieved by the DataFunction. |
| DurationUnits | string | A code that indicates what the duration unit is. For example: 'day', 'single event', etc. |
| Duration | Integer | The number of units the permission is being granted for. |
| Description | String | A detailed description of the permission. |

In another embodiment, one or more of the following PropertyPermission Property Collection attributes can be used during this process:

| Name | Type | Description |
| --- | --- | --- |
| Include | Boolean | A Boolean value, which indicates if the property should be included (True) or excluded (False) |
| GPP | string | The GPP of a property within the Entity to which the permissions apply. |

READ PERMISSION EXAMPLE: Drug XYZ and Heart Rate Data

In one exemplary embodiment, a patient grants the following read access to Drug Company XYZ for Drug XYZ:
1. Patients birthdate
2. Patients zip
3. Patients gender
4. Patients allergies
5. Patients genomics
6. Patients Prescriptions/transactions for Drug XYZ
    a. Once the transactions for Drug XYZ are known, the ReadDataFunction can determine the While_On_Drug_XYZ (Date range), which will be used within other GPP data queries.
7. Patients Exercise Data
    a. While_On_Drug_XYZ (+/−X Days)
    b. Data
        i. Start Date/Time
        ii. End Date/Time
        iii. Description (i.e. running, walking, lifting, yoga)
8. Patients Apple watch Heart Rate data
    a. While_On_Drug_XYZ (+/−X Days)
    b. Data (i.e. predefined function)
        i. 10-minute intervals
        ii. Mean
        iii. Low
        iv. High Such permissioning can be more than just giving access to data items. It can be giving access to different types of data based on the date range of prescription transactions. Because of the complexity of defining the sub queries (e.g., heart rate data, etc.) as independent queries, a set of predefined functions that understand how to retrieve the data of interest can be implemented. Once a specific function is instantiated, the system can reference the function as part of the permission. These functions can be stored on the blockchain (e.g., in a catalog) with a description of what they do.

Figure 4:
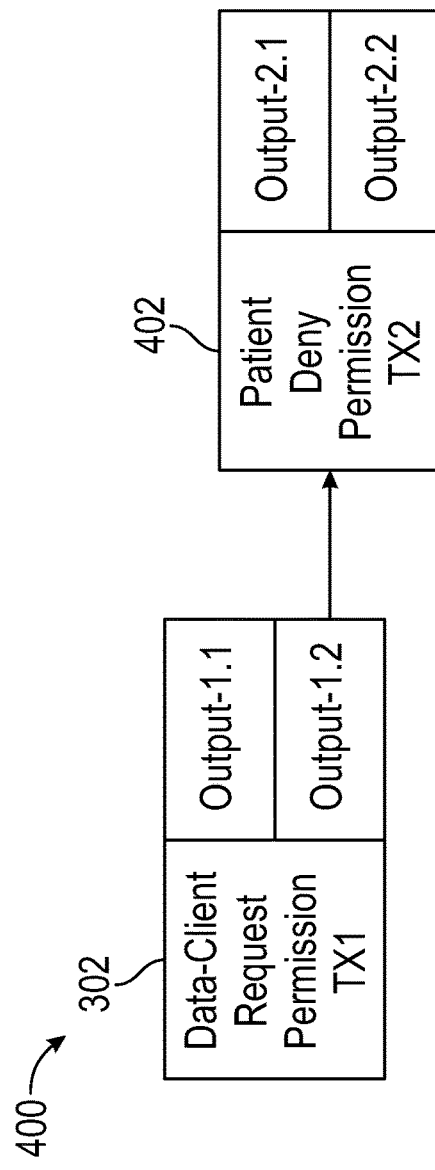
FIG. 4 illustrates a data request-deny schematic, in accordance with one or more exemplary embodiments of the present disclosure.

FIG. 4 illustrates a data request-deny schematic 400, in accordance with one or more exemplary embodiments of the present disclosure. In one embodiment, the Patient has the ability to 'deny' permission to read data for a specific entity, and specific properties within that entity, from their GPR. For example, if the Patient decides to deny the permission, the permissioning module can process data as follows: generation of a Data-Client Request Permission blockchain transaction (TX1) 302 having an Output-1.1 and Output-1.2; and generation of a Patient Deny Permission blockchain transaction (TX2) 402 having an Output-2.1 and Output-2.2.

In another embodiment, if the Patient decides to deny the permission, the permissioning module can issue another blockchain transaction (TX2) 402, with two outputs, which spends Output-1.2 of TX1 302. The Output-2.1 can be a data output, which contains a Property Collection (PC) with property values that specify that the permission has been denied. The Output-2.2 can send the change of the transaction or a notification thereof to the Patient.

Figure 5:
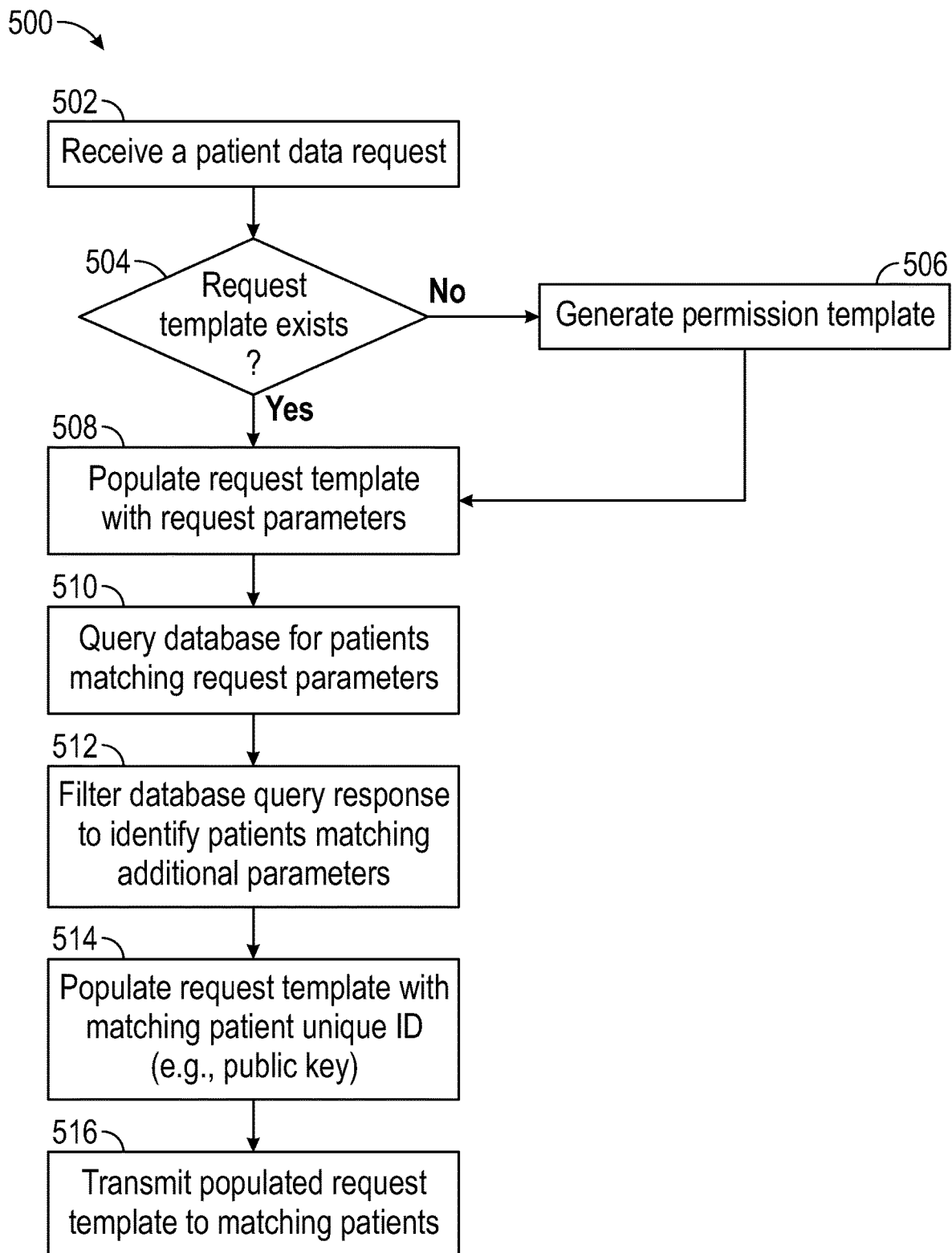
FIG. 5 illustrates a flowchart exemplifying permission request control logic, in accordance with one or more exemplary embodiments of the present disclosure.

FIG. 5 illustrates a flowchart exemplifying permission request process flow control logic 500, in accordance with one or more exemplary embodiments of the present disclosure. The request process flow control logic 500 can be implemented as an algorithm on a server 102, a machine learning module, a client 150, a memory 130, a combination of one or more of the aforementioned components, or other suitable system. The request process flow control logic 500 can be achieved with software, hardware, an application programming interface (API), a network connection, a network transfer protocol, HTML, DHTML, JavaScript, Dojo, Ruby, Rails, other suitable applications, or a suitable combination thereof.

The request process flow control logic 500 can leverage the ability of a computer platform to spawn multiple processes and threads by processing data simultaneously. The speed and efficiency of the request process flow control logic 500 can be greatly improved by instantiating more than one process to implement a permission request. However, one skilled in the art of programming will appreciate that use of a single processing thread may also be utilized and is within the scope of the present disclosure.

Since patients may not interact directly with companies interested in acquiring their data, there can be a mechanism that can allow a request to be sent to the patient with a clear understanding of the following:

What the data will be used for.
The date range, if applicable, for the request.
The data elements for which permission is being requested.
The process of collecting the data.
The date range, the permission will be valid.

When a company such as Drug Company XYZ, wants to gain access to data, they can submit a request, provide a description, and determine if a predefined Permission Template already exists for the type of request.

The request process flow control logic 500 of the present embodiment begins at step 502, where the control logic 500 can generate or receive a patient data access request. In one embodiment, the request can be from a client. In another embodiment, the request can include request data having one or more fields, parameters, characteristics, or metadata. For example, the patient access request can include healthcare parameters, pharmaceutical parameters, clinical parameters, demographic parameters, time parameters, volume parameters, frequency parameters, or other relevant parameters. In another exemplary embodiment, the request can include a command such as upload, download, save, retrieve, or other suitable command. The control logic 500 then proceeds to step 504.

At step 504, the control logic 500 can determine whether a request template exists. In one embodiment, the request template can be retrieved from the blockchain. For example, the request template can be stored in a catalog of templates (e.g., Read Permission Request Catalog) stored in the blockchain. If a request template exists, the control logic 500 proceeds to step 508. If the request template does not exist, the control logic proceeds to step 506.

At step 506, the control logic 500 can generate a permission template including at least a portion of the data from the request. In one embodiment, the template can have a standardized set of fields or parameters based upon the request. In another embodiment, the template can transform the request into a standardized format processable by the system. In another embodiment, a permission template can be generated listing the requirements of the request. In another embodiment, the requirements can be written and packaged as a data retrieval function and installed on a decrypt server. This function can be added to the new template. The finalized permission request template can be stored in a request catalog (e.g., on the blockchain). The control logic 500 then proceeds to step 508.

At step 508, the control logic 500 can populate request template with request parameters. In one embodiment, the control logic 500 can parse the request to populate one or more corresponding fields in the template. For example, the template can have a standardized set of fields or parameters based upon the request. In another embodiment, the control logic can use the template to transform the request into a standardized format processable by the system. The control logic 500 then proceeds to step 510.

At step 510, control logic 500 can query a database for patients matching the request parameters. In one embodiment the control logic 500 can generate a query response with a listing of patients matching the query. The control logic 500 then proceeds to step 512.

At step 512, the control logic 500 can filter a database query response to identify patients matching additional parameters or narrow the list of patients according to the additional parameters. In one embodiment, not enough patients are returned matching the query so the control logic 500 can widen the search by adding additional parameters to the query. For example the thresholds for the number of query returns and the additional parameters can be included in the request. In another embodiment, too many patients are returned matching the query so the control logic 500 can narrow the search by adding additional parameters to the query. The control logic 500 then proceeds to step 514.

At step 514, the control logic 500 can populate a request template having a matching patient unique ID (e.g., public key). In one embodiment, The template can be populated with the relevant properties for the request. The GPR Database (e.g., BC RAW DB) can be queried to identify the patients that match the requirements of the request. In another embodiment, for each patient that qualifies: The template will be populated with the Public Key of the patient and the 'ReadPermissionRequest' can be transmitted to the patient. The control logic then proceeds to step 516.

At step 516, the control logic 500 can transmit a populated request template to matching patients. In one embodiment, the request template can identify the types of data for which access is requested. In another embodiment, the request template can indicate an offer amount for access to the requested data. The control logic 500 then terminates or awaits a new request and can repeat the aforementioned steps.

In one embodiment, a GPR data read permission request can include:

| Property Name | Type | Description |
| --- | --- | --- |
| RID | String | A GUID that will be used as the ID for the read permission request. |
| Description | String | A Description of the data that is being requested. |
| Duration_Unit | String | A code that indicates the requested duration unit. For example: 'day', 'single event', etc. |
| DurationUnits | string | A code that indicates what the duration unit is. For example: 'day', 'single event', etc. |

In one embodiment, a GPR data read permission response can include:

| Property | Example Value | |
| --- | --- | --- |
| GPP | Patient.Prescriptions | Grant read access to the patient's prescriptions. |
| GPP_Filter | Drug_XYZ | The name of a 'filter' that limits the 'result set' of the GPP to only be prescriptions that were written for Drug XYZ. |
| GPP_Filter_Result_Set | drug_xyz_rs | The name of the result set |

In one embodiment, the control logic 500 can have built-in functions. For example, the control logic 500 can assign a name to the 'result set,' having the 'drug_xyz_rs.values,' which can be the collections of RxTx collections and the drug. In another embodiment, control logic 500 can execute a collection of functions that can determine, for example, the date range—given a list of prescription transactions. The result set can be a predefined or dynamic PC. The control logic can execute SQL commands to filter the results set, for example: select min (date_of_service) from 'result set' and select max(date_of_service) from 'result set.' For example, the GPP can be the address of the data; the GPP_Filter can be a predefined filter that can consider all PCs of GPP and produce a result set. The result set functions can be a collection of filter creation functions. Given a result set, the control logic 500 can run a function that can create a Filter, that can be used to 'filter' other data sets. In another embodiment, the control logic 500 can define functions that return a dynamic filter and store them on the blockchain. For example, Filter While_On_Drug_XYZ=DetermineMinMax(result_set).

Figure 6:
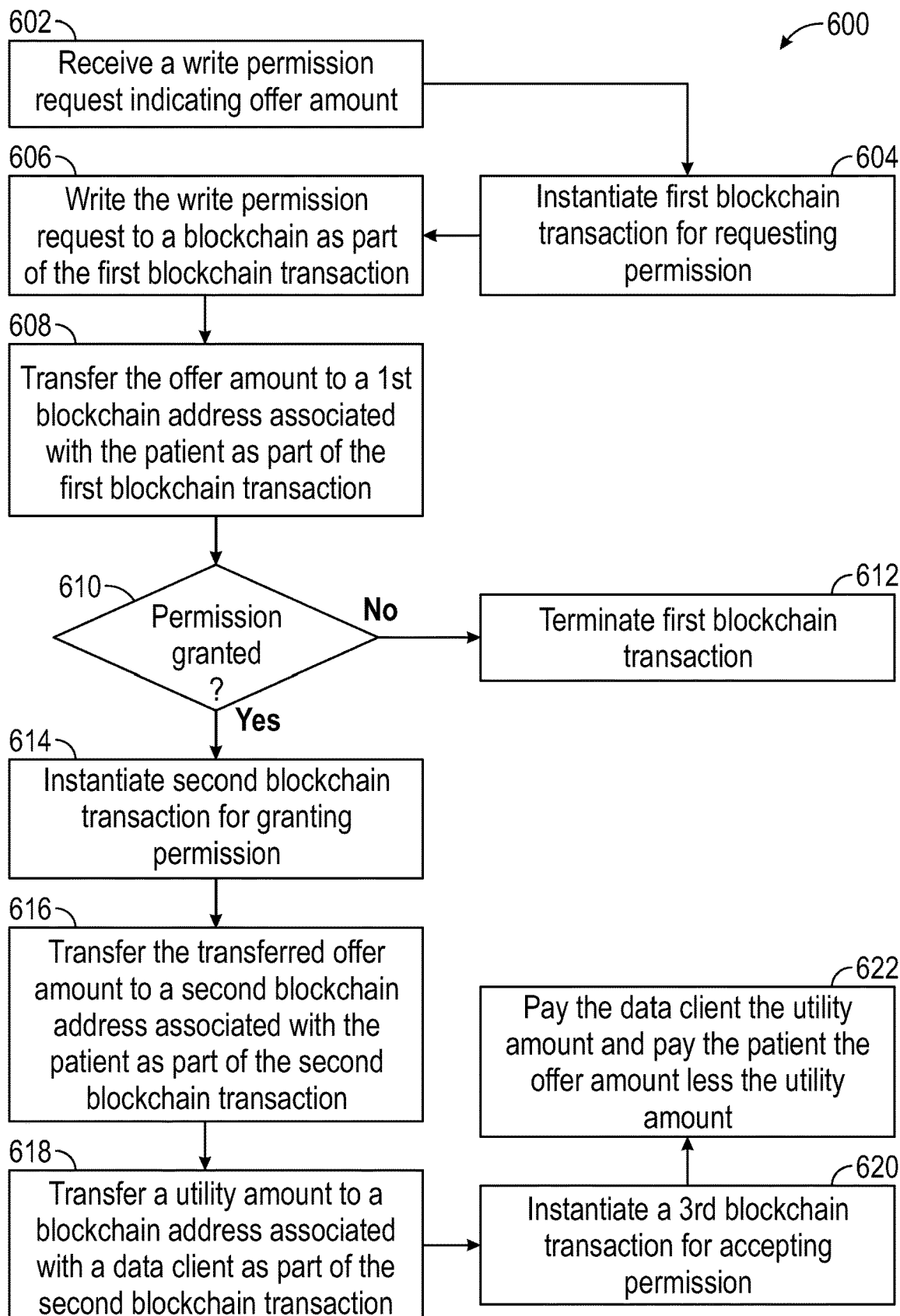
FIG. 6 illustrates a flowchart exemplifying data write request control logic, in accordance with one or more exemplary embodiments of the present disclosure.

FIG. 6 illustrates a flowchart exemplifying data write request process flow control logic 600, in accordance with one or more exemplary embodiments of the present disclosure. The data write request process flow control logic 600 can be implemented as an algorithm on a server 102, a machine learning module, a client 150, a memory 130, a combination of one or more of the aforementioned components, or other suitable system. The data write request process flow control logic 600 can be achieved with software, hardware, an application programming interface (API), a network connection, a network transfer protocol, HTML, DHTML, JavaScript, Dojo, Ruby, Rails, other suitable applications, or a suitable combination thereof.

The data write request process flow control logic 600 can leverage the ability of a computer platform to spawn multiple processes and threads by processing data simultaneously. The speed and efficiency of the data write request process flow control logic 600 can be greatly improved by instantiating more than one process to implement a data write request. However, one skilled in the art of programming will appreciate that use of a single processing thread may also be utilized and is within the scope of the present disclosure.

In one embodiment, a Data-Write-Permission request can be a 'Property Collection' (PC) containing specific properties that describe the write permission rights and an amount the Data-Client is willing to offer for the Data-write-Permission rights. In one embodiment, this PC can be written as part of a blockchain transaction (TX1) (e.g., Bitcoin-SV), which can be issued by the Data-Client, as Output-1.1. The TX1 transaction can have a second output (Output-1.2) that can pay an enticement to consider offer amount to the blockchain address of the Patient, from which the Data-Client is seeking permission. If the Patient decides to grant the permission, the Patient can issue another blockchain transaction (TX2) that can spend Output-1.2 of TX1 and pay a nominal amount to the Data-Client through Output-2.2. The TX2 transaction can also send money to another blockchain address of the Patient (e.g., spending the enticement to consider amount). The Data-Client can then write another blockchain transaction (TX3), which can spend Ouput-2.2 of TX2 and pay the Patient the offer amount for the Data-Read-Permission. These blockchain transactions can represent the Data-Write-Permission Contract between the Data-Client and the Patient. This contract can be verified when the Data-Client issues a data write request associated with the Data-Write-Permission.

The request process flow control logic 600 of the present embodiment begins at step 602, where the control logic 600 can receive a write permission request indicating an offer amount. In one embodiment, the request can be from a client. In another embodiment, the request can include request data having one or more fields, parameters, characteristics, or metadata. For example, the patient access request can include healthcare parameters, pharmaceutical parameters, clinical parameters, demographic parameters, time parameters, volume parameters, frequency parameters, or other relevant parameters. In another exemplary embodiment, the request can include a command such as upload, download, save, retrieve, or other suitable command. The control logic 600 then proceeds to step 604.

Add step 604, the control logic 600 can instantiate a first blockchain transaction for requesting permission. The control logic 600. Then proceeds to step 606.

At step 606, the control logic 600 can write the write permission request to a blockchain as part of the first blockchain transaction. The control logic then proceeds to step 608.

Add steps 608, the control logic 600 can transfer the offer amount to a first blockchain address associated with the patient as part of the first blockchain transaction. In one embodiment, a patient can have one or more blockchain addresses associated with the patient. For example, each blockchain entry having a unique ID associated with the patient can have an address, that address can be associated with the patient via the unique ID. The control logic 600 then proceeds to step 610.

At step 610, the control logic 600 can determine whether permission was granted. If permission was not granted, the control logic 600 proceeds to step 612. If permission was granted, the control logic 600 proceeds to step 614.

At step 612, the control logic 600 can terminate the first blockchain transaction. The control logic 600 can then terminate or await a new request and repeat the aforementioned steps.

At step 614, the control logic 600 can instantiate a second blockchain transaction for granting permission. The control logic 600 then proceeds to step 616.

At step 616, the control logic 600 can transfer the transferred offer amount to a second blockchain address associated with the patient as part. Of the second blockchain transaction. The control logic 600 then proceeds to step 618.

At step 618, the control logic 600 can transfer a utility amount to a blockchain address associated with a data client or utility as part of the second blockchain transaction. The control logic 600 then proceeds to Step 620.

At step 620, control logic 600 can instantiate a third blockchain transaction for accepting permission. The control logic 600 then proceeds to step 622.

At step 622, the control logic 600 can pay the data client or the utility the utility amount and pay the patient the offer amount less the utility amount. The control logic 600 can then terminate or await a new request and repeat the aforementioned steps.

In another embodiment, a Write Permission Property Collection can include the following:

| Name | Type | Description |
| --- | --- | --- |
| Type | String | "w"-Read |
| PublicKey | byte array | A public key representing an ID for the patient. The patient's root public key is not exposed. |
| GPP | string | The GPP of the entity in which the permission applies. |

| Name | Type | Description |
|---|---|---|
| GPP_Children | Boolean | A Boolean value that indicates if the permission is being granted to all child nodes of the GPP. |
| FromDateTime | DateTime | A DateTime value used to indicate the minimum Date and Time of when the write permission starts. If this field is not present, then write permission starts immediately. |
| ToDateTime | DateTime | A DateTime value used to indicate the maximum Date and Time of the write permission is effective. If this property is not present the write permission is indefinite. |
| DurationUnits | string | A code that indicates what the duration unit is. For example: 'day', 'single event', etc. |
| Duration | Integer | The number of units the permission is being granted for. |
| Description | String | A detailed description of the permission. |

Figure 7:
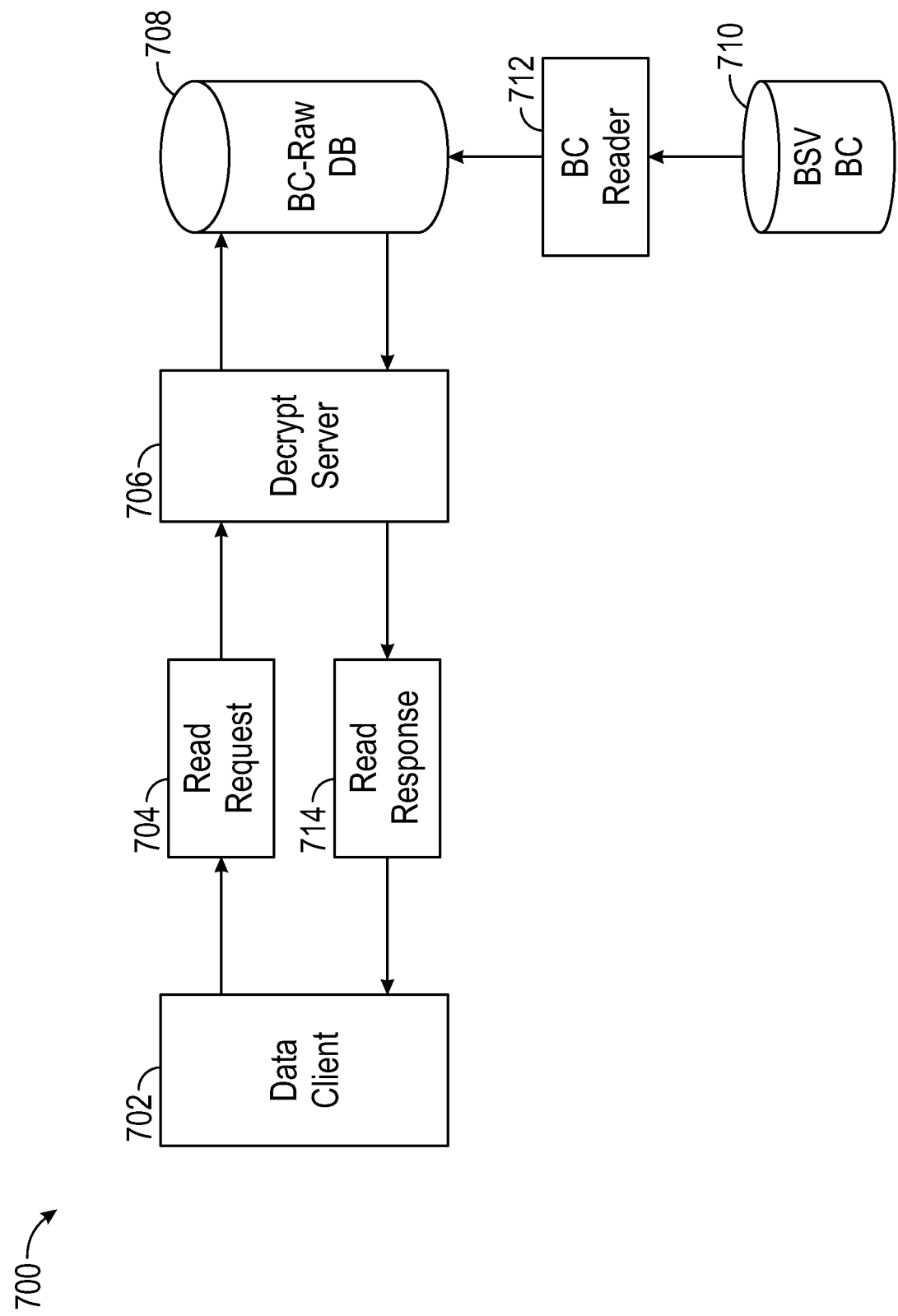
FIG. 7 illustrates an electronic health record data read system schematic, in accordance with one or more exemplary embodiments of the present disclosure.

FIG. 7 illustrates an electronic health record data read system 700 schematic, in accordance with one or more exemplary embodiments of the present disclosure. The electronic health record data read system 700 can include a data client 702, a decrypt server 706, a GPR database 708, a blockchain reader 712, and a blockchain 710. In one embodiment, the data client 702 can be a client 150, the decrypt server can be a server 102, the GPR database can be a memory 130, the block chain reader 712 can be a transaction blockchain API 110, and the blockchain can be a memory 130. For example, a Data-Client can be a software component that requests data to be queried and returned based on a preexisting and valid read permission contract; a Read Request can be a message that can request GPR entity data to be queried and returned; a Read Response can be the requested GPR decrypted data; a Decrypt Server can be responsible for looking up the predefined permission request by querying the BC-RAW DB for the entities covered by a preexisting and valid read permission contract; a BC-RAW DB can be a database that contains GPR Entity data—the data within this database can be encrypted; a BC-Reader can read blocks from the Blockchain, processes each transaction within the block and determine if the transaction contains GPR data—if the transaction does contain GPR data, the data can be loaded into the BC-Raw DB; and a BSV BC can be the Blockchain.

Since at least a portion of the data within the GPR can be encrypted it can remain encrypted until it is requested. The decrypt server can be used to decrypt data from the GPR database (e.g., BC-Raw DB). The decrypt server can be encrypt and decrypt data using PGP, Blowfish, Twofish, AES, 3DES, HTTPS, or other suitable encryption standards. The data in the BC-Raw DB 708 may have been previously read from the Blockchain 710 (e.g., BSV BC).

In another embodiment, when the Decrypt Server 706 receives a Read Request 704, it determines if the sender is authorized to submit the request. For example, the authorization can be performed by checking a digital signature that may be provided with the request. In another embodiment, once the request has been authorized, the Decrypt Server 706 queries the BC-RAW DB 708 for the GPR entities that were defined by a preexisting and valid permission contract. In another embodiment, once the entities have been retrieved, each entity can be decrypted using the Private Key of the node where it was stored in the blockchain 710 (e.g., Metanet Tree within the Bitcoin SV blockchain). Once the entity has been decrypted, the serialized byte array can be returned to the client in the Decrypt Response.

Although one or more embodiments may reference a patient, the present disclosure applies to any type of entity, whether a person, patient, customer, company, or other suitable entity capable of having data stored in a record associated with that entity. Similarly, although certain embodiments may reference electronic health records, the systems, methods, and concepts disclosed herein are equally applicable to any storage system or record type.

Persons skilled in the art will readily understand that advantages and objectives described above would not be possible without the particular combination of computer hardware and other structural components and mechanisms assembled in this inventive system and described herein. Additionally, the algorithms, methods, and processes disclosed herein improve and transform any general-purpose computer or processor disclosed in this specification and drawings into a special purpose computer programmed to perform the disclosed algorithms, methods, and processes to achieve the aforementioned functionality, advantages, and objectives. It will be further understood that a variety of programming tools, known to persons skilled in the art, are available for generating and implementing the features and operations described in the foregoing. Moreover, the particular choice of programming tool(s) may be governed by the specific objectives and constraints placed on the implementation selected for realizing the concepts set forth herein and in the appended claims.

The description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f). Even under the broadest reasonable interpretation, in light of this paragraph of this specification, the claims are not intended to invoke 35 U.S.C. § 112(f) absent the specific language described above.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A system for record access permissioning and monetization, comprising:
   a blockchain storing one or more data records; and
   a computer processor operably coupled to the blockchain and capable of executing machine-readable instructions to perform program steps, the program steps comprising:
   receiving a write permission request from a client indicating types of data to be accessed and an offer amount for access;
   instantiating a first blockchain transaction for requesting access permission to a person's record, wherein the first blockchain transaction generates a first output;
   writing the write permission request to the blockchain as part of the first block chain blockchain transaction;
   transferring the offer amount to a first blockchain address associated with the person as part of the first block chain-blockchain transaction;
   determining that permission to access a record was granted by the person and instantiating a second blockchain transaction for granting permission, wherein the first output is input into the second blockchain transaction and the second blockchain transaction generates a second output;
   instantiating a third blockchain transaction for accepting permission, wherein the second output is input into the third blockchain transaction; and
   paying the person the offer amount.

2. The system of claim 1, wherein the program steps further comprise transferring the offer amount having the first blockchain address to a second blockchain address associated with the patient as part of the second blockchain transaction.

3. The system of claim 1, wherein the program steps further comprise transferring a utility amount to a blockchain address associated with a data client as part of the second blockchain transaction.

4. The system of claim 3, wherein the person is paid the offer amount less the utility amount.

5. The system of claim 1, further comprising a transaction blockchain API configured to provide access to data stored on the blockchain.

6. The system of claim 5, wherein the transaction blockchain API includes an interface that defines interactions between multiple components.

7. The system of claim 1, wherein the write permission request is a Property Collection (PC).

8. The system of claim 7, wherein the write permission request Property Collection contains the write permission rights.

9. The system of claim 7, wherein the write permission request Property Collection contains the offer amount.

10. The system of claim 1, further comprising a wallet module configured to facilitate an electronic financial transaction over an encrypted network.

11. A method of record access permissioning and monetization, comprising:
    receiving a write permission request from a client indicating types of data to be accessed and an offer amount for access;
    instantiating a first blockchain transaction for requesting access permission to a person's record, wherein the first blockchain transaction generates a first output;
    writing the write permission request to a blockchain as part of the first block-hain blockchain transaction;
    transferring the offer amount to a first blockchain address associated with the person as part of the first blockchain transaction;
    determining that permission to access a record was granted by the person and instantiating a second blockchain transaction for granting permission, wherein the first output is input into the second blockchain transaction and the second blockchain transaction generates a second output;
    instantiating a third blockchain transaction for accepting permission, wherein the second output is input into the third blockchain transaction; and
    paying the person the offer amount.

12. The method of claim 11, further comprising transferring the offer amount having the first blockchain address to a second blockchain address associated with the patient as part of the second blockchain transaction.

13. The method of claim 11, further comprising transferring a utility amount to a blockchain address associated with a data client as part of the second blockchain transaction.

14. The method of claim 13, wherein the person is paid the offer amount less the utility amount.

15. The method of claim 11, further comprising a transaction blockchain API configured to provide access to data stored on the blockchain.

16. The method of claim 15, wherein the transaction blockchain API includes an interface that defines interactions between multiple components.

17. The method of claim 11, wherein the write permission request is a Property Collection (PC).

18. The method of claim 17, wherein the write permission request Property Collection contains the write permission rights.

19. The method of claim 17, wherein the write permission request Property Collection contains the offer amount.

20. The method of claim 11, further comprising a wallet module configured to facilitate an electronic financial transaction over an encrypted network.

* * * * *